(12) United States Patent
Tinwala et al.

(10) Patent No.: US 7,558,367 B1
(45) Date of Patent: Jul. 7, 2009

(54) METHOD AND SYSTEM FOR DETECTING BREAST LATERALITY

(75) Inventors: On Ali Tinwala, Gujarat (IN); Mehul Satishkumar Kapadia, Gujarat (IN)

(73) Assignee: General Electric Co., Schenectady, NY (US)

( * ) Notice: Subject to any disclaimer, the term of this patent is extended or adjusted under 35 U.S.C. 154(b) by 0 days.

(21) Appl. No.: 12/119,953

(22) Filed: May 13, 2008

(51) Int. Cl.
*A61B 6/04* (2006.01)
(52) U.S. Cl. ........................................ 378/37
(58) Field of Classification Search ............ 378/37, 378/62
See application file for complete search history.

(56) References Cited

U.S. PATENT DOCUMENTS 7,146,031 B1    12/2006    Hartman et al.
2004/0234125 A1    11/2004    Menhardt et al.
2008/0043904 A1    2/2008    Hoernig
2008/0049996 A1    2/2008    Marshall et al.
2008/0069416 A1    3/2008    Luo

FOREIGN PATENT DOCUMENTS

WO    WO 2006/129498    12/2006

*Primary Examiner*—Courtney Thomas

(57) ABSTRACT

A method for determining breast laterality includes interpreting laterality of a breast using at least one patient parameter obtained from orientation of a patient with reference to an axis. Some of the patient parameters include patient position, patient head orientation and patient's weight distribution. The patient parameters are identified with reference to the center of the breast being imaged. A system for performing this method for determining breast laterality is also described.

15 Claims, 13 Drawing Sheets

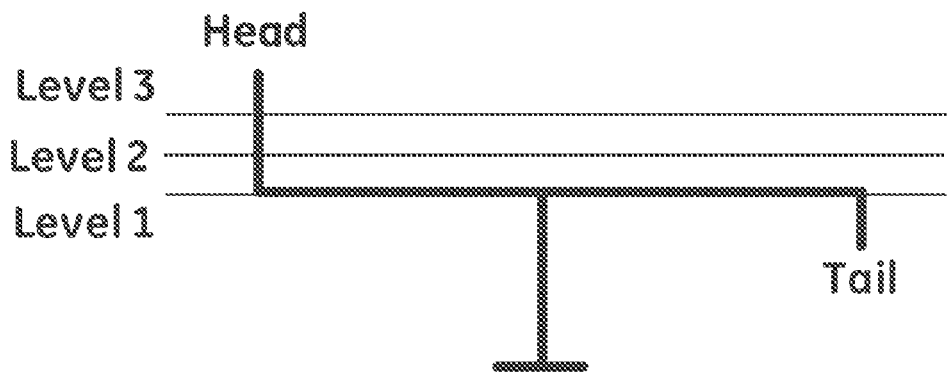
FIG. 7A
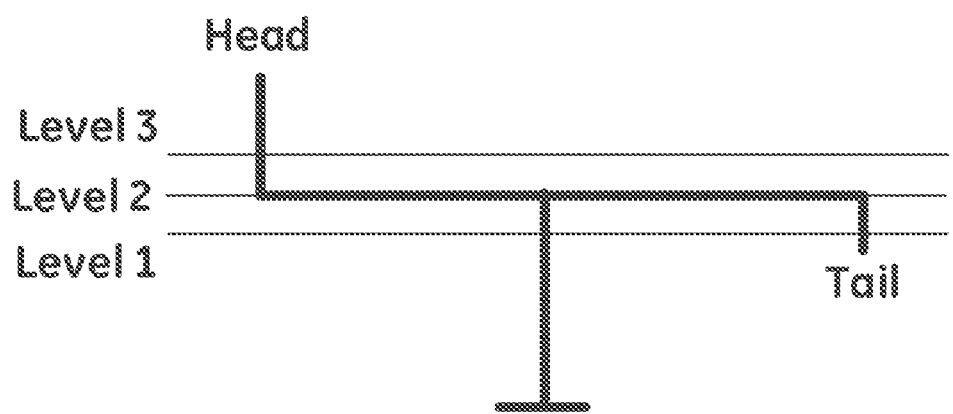
FIG. 7B
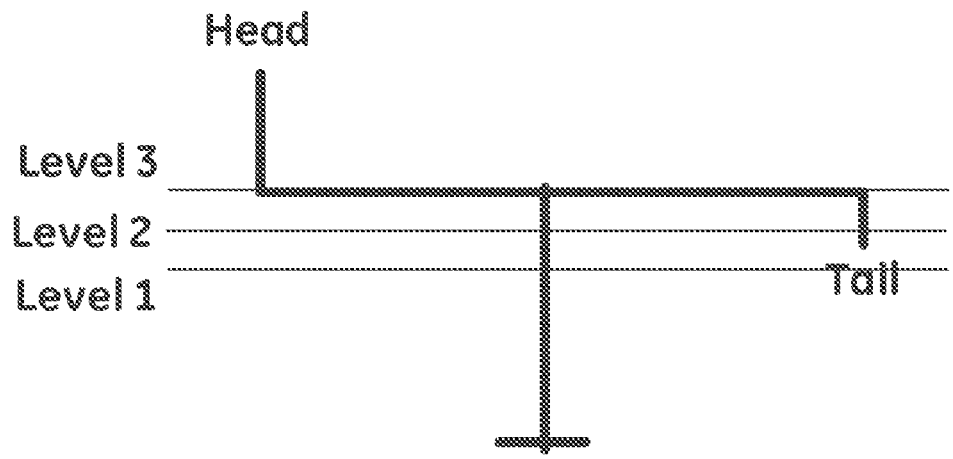
FIG. 7C
| Breast Laterality | Table Level | | |
|---|---|---|---|
| | Level 1 | Level 2 | Level 3 |
| Table Head End to Left | Left Breast | Both Breasts | Right Breast |
FIG. 7D

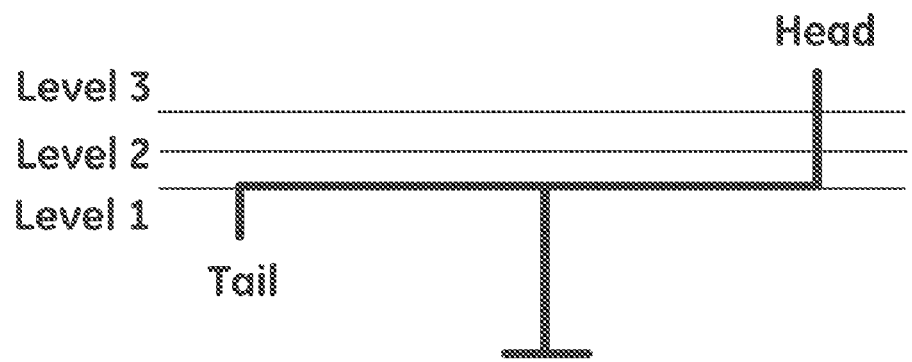
FIG. 8A
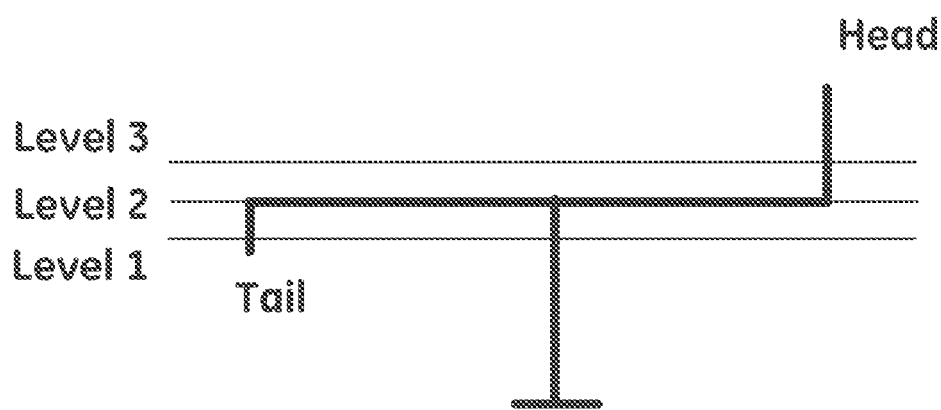
FIG. 8B
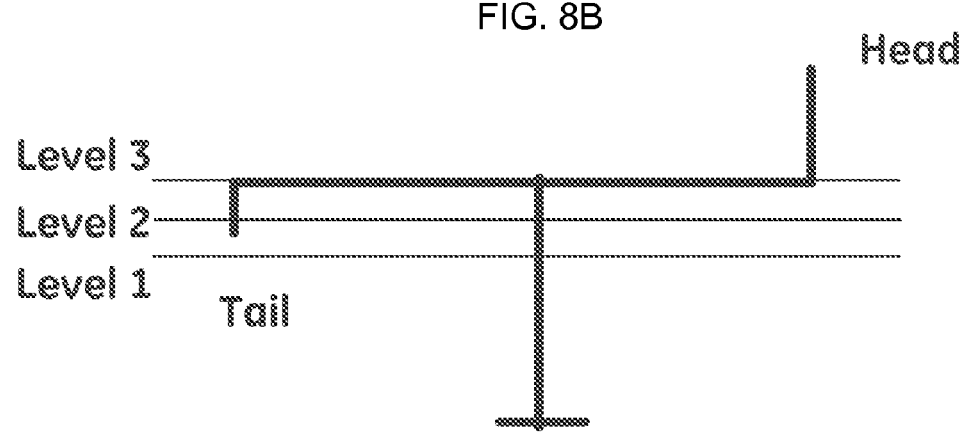
FIG. 8C
| Breast | Table Level | | |
| Laterality | Level 1 | Level 2 | Level 3 |
| Table Head End to Right | Left Breast | Both Breasts | Right Breast |
FIG. 8D

| Breast Laterality | H | | |
|---|---|---|---|
| | Level 1 | Level 2 | Level 3 |
| Head Left | Left Breast | Both Breasts | Right Breast |
| Head Right | Right Breast | Both Breasts | Left Breast |

METHOD AND SYSTEM FOR DETECTING BREAST LATERALITY

FIELD OF THE INVENTION

This invention relates generally to mammography methods and systems, and more particularly to, a method and system for detecting laterality of breasts in a mammography procedure.

BACKGROUND OF THE INVENTION

Mammography has earned great deal of significance, as it's a method for detecting signs of breast cancer. In a conventional mammography view, two views are obtained for each breast namely a craniocaudal (CC) view obtained by positioning the X-ray film horizontally under the compressed breast, and a medio-lateral oblique (MLO) view obtained by positioning X-ray film orthogonally to left-right axis. Thus for both the breasts together there are four view taken, typically named as LCC (Left craniocaudal), RCC (Right craniocaudal), LMLO (Left medio-lateral oblique) and RMLO (Right medio-lateral oblique). For an appropriate review of the images, it is essential to know the type of view and laterality of the breasts.

To assist in review process, the type of view and the laterality is mentioned in a particular format in the images. Conventionally an operator manually enters the laterality to the mammography system or to the processing circuitry associated with the system. The system incorporates this information to the images after the imaging is done. Since there is no mechanism to check whether the operator has entered the data correctly, it is desired to have a mechanism to ensure that the operator has entered the correct laterality, or a method to automatically determine the laterality of the breasts without human intervention.

There exist some algorithmic solutions that detect breast laterality from the image. The laterality is verified after the imaging. Also some of the existing solutions suggest a method to correct the laterality at a later stage, if the operator realizes his mistake later. Thus it will be beneficial to have a simple, economical solution to automatically identify the laterality before imaging or while imaging the patient.

Also some times due to patient's medical condition or due to some other reason, the patient may not be able to stand in front of the scanner for imaging. It will be difficult to identify the laterality of the breasts in the recumbent position.

Thus there exists a need to provide a method and system for automatically detecting the breast laterality in a mammography imaging procedure even while the patient is in the recumbent position.

SUMMARY OF THE INVENTION

The above-mentioned shortcomings, disadvantages and problems are addressed herein which will be understood by reading and understanding the following specification.

One embodiment of the present invention provides a method of determining breast laterality. The method comprises: interpreting breast laterality using at least one patient parameter indicating the orientation of a patient with reference to an axis.

In another embodiment, a mammography imaging system with automatic laterality detection is disclosed. The system comprises: a scanner; a detachable, patient parameter identifier attached to the scanner, the patient parameter identifier configured to detect a patient parameter based on the orientation of a patient with respect to an axis; and a processor configured to interpret breast laterality based on the patient parameter.

In yet another embodiment, a mammography imaging system with automatic laterality detection is disclosed. The system comprises: a scanner; a detachable sensor assembly having one or more sensors connected to the scanner, and configured to detect the position of a patient with reference to an axis; and a processor configured to interpret breast laterality based on the position of the patient.

In yet another embodiment, a mammography imaging system with automatic laterality detection is disclosed. The system comprises: a scanner; a patient weight measuring assembly attachable to the scanner, and configured to detect the distribution of a patient's weight with respect to an axis; and a processor configured to interpret laterality of the patient based on the weight distribution of the patient.

In yet another embodiment, a mammography imaging system with automatic laterality detection is disclosed. The system comprises: a scanner having an adjustable breast positioner; an adjustable patient table attachable to the scanner, providing direction of head of a patient and location of a patient with reference to ground level; and a processor configured to interpret laterality of the patient based on the orientation of the patient.

Various other features, objects, and advantages of the invention will be made apparent to those skilled in the art from the accompanying drawings and detailed description thereof.

BRIEF DESCRIPTION OF THE DRAWINGS

FIGS. 7A to 7D illustrate various positions of an adjustable patient table and laterality table indicating the laterality based on the table position as described in an embodiment of the invention;

FIGS. 8A to 8D illustrate various positions of an adjustable patient table and laterality table indicating the breast laterality based on the table position as described in an embodiment of the invention;

DETAILED DESCRIPTION OF THE INVENTION

Figure 1:
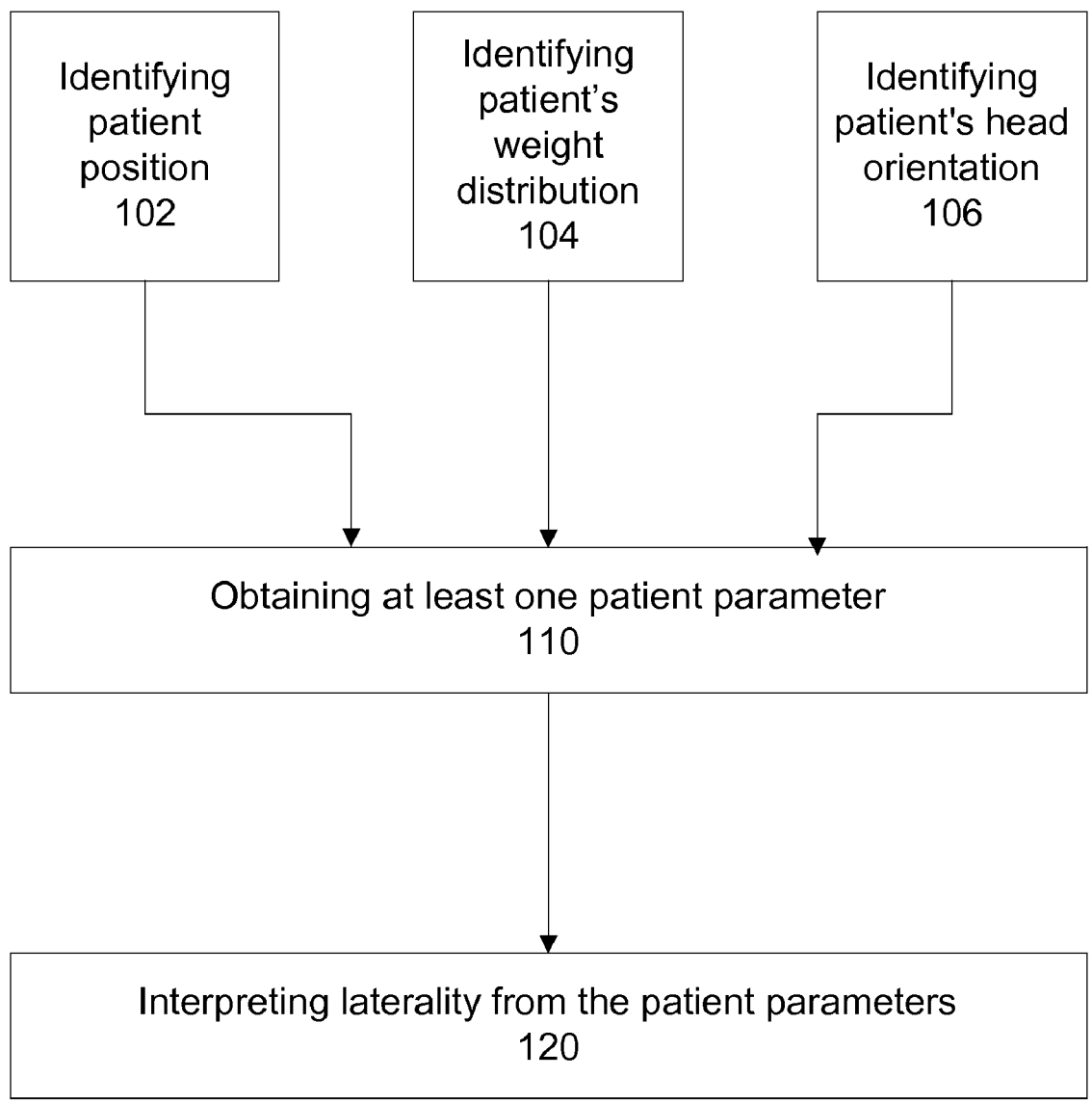
FIG. 1 is a flowchart illustrating a method of determining laterality of breast in a mammography procedure as described in an embodiment of the invention.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Various embodiments of the present invention are directed to methods and systems for automatically detecting laterality of breast in mammography. The laterality is detected before the imaging or while imaging. The laterality is determined automatically, thereby eliminating human intervention and increasing accuracy. The laterality is detected based on the orientation of the patient towards left or right with reference to an axis. If one side of the patient is being imaged, the rest of the body of the patient will be lying towards the other side and based on this laterality is determined.

In an embodiment, the laterality of the breast is determined using a patient's position. The position of the patient is identified using a patient position identifier. The sensor assembly could be a detachable mechanism attached to a non-moving surface. In an example, the sensor assembly is attached to a stationary part of the scanner or to the roof or ceiling above the scanner.

In an embodiment, the laterality is detected based on distribution of a patient's weight with respect to an axis. Based on the distribution of patient's weight towards left or right, laterality is detected. In an example a pedal assembly is used to determine the laterality.

In an embodiment the laterality of a patient in the recumbent position is determined. The laterality in an example is determined using the location of the patient's body and the orientation of the patient's head with reference to an axis.

The laterality is determined before the imaging or while imaging.

In an embodiment various error correction techniques are proposed for correcting the error that could occur while determining the laterality due to changes in the axis. In an example, the patient parameter identifier is adjusted in accordance with gantry movement in the imaging system.

In an embodiment, the feature of automatically determining the laterality may be provided as an optional feature. Also priority can be set between the laterality input from an operator or from the automatic detection mechanism. The automatic laterality detection mechanism may be used as a laterality verification technique with respect to the laterality entered by the operator.

Although the invention is explained with reference to patient parameter including patient weight and patient location including head orientation, the laterality may be detected using other patient parameters as well, including temperature or any other physiological parameter for each breast while imaging.

FIG. 1 is a flowchart illustrating a method of determining laterality of breast in a mammography procedure as described in an embodiment of the invention. At step 110, at least one patient parameter is obtained. Patient parameters are obtained with reference to a fixed axis. In an embodiment, the patient parameter is position of a patient, and is obtained at step 102. The patient position is a relative measure indicating whether the patient body is lying towards left or right. Hence the patient position is determined with reference to a fixed axis. In another embodiment, the patient parameter is distribution of weight of patient with reference to an axis determined as at step 104. The weight distribution of the patient is identified with reference to an axis i.e weight is more towards the left side of the axis or towards the right side. In another embodiment, the patient parameter is the orientation of patient head with reference to an axis along with the location of the body, as determined at step 106.

As mentioned, at step 110, the patient parameter is obtained by at least one of the step 102, 104 and 106. At step 120, the laterality is interpreted from the patient parameter obtained. In an embodiment, the patient parameter obtained is a patient location with reference to the axis. This indicates that the patient body is aligned towards left or right with reference to an axis. The concept used is if the left breast of the patient is being imaged, the rest of the patient body will be lying towards right and if the right breast is being imaged, the body will be lying towards left. Based on the same the laterality of the patient may be determined. In an embodiment, if the patient parameter is weight of the patient, the distribution of the patient weight with respect to an axis is obtained. The laterality can be interpreted based on the fact that if the right side of the patient is being imaged, the weight of the patient will be lying towards the left side and if the left side is being imaged, the patient weight will be lying towards the right. In an embodiment, the patient head orientation is obtained as the patient parameter. If the patient head orientation is obtained along with the patient's body location such as height of breast from the ground level, or the position of the breast with reference to a breast positioner located at the scanner. From this information, the laterality of the breast can be interpreted. In an example, the breast laterality is determined by taking the center of the breast being imaged as the axis.

Figure 2:
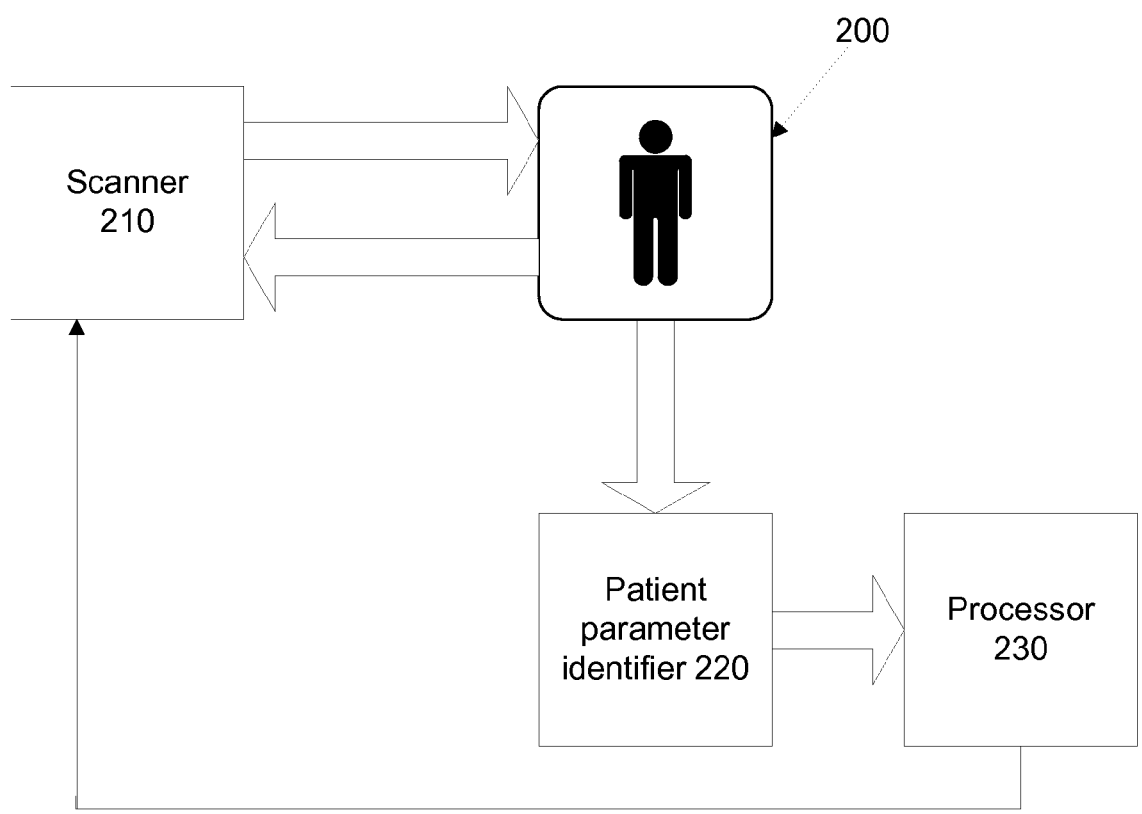
FIG. 2 is block diagram of a mammography imaging system with automatic breast laterality detection as described in an embodiment of the invention.

FIG. 2 is block diagram of mammography imaging system with automatic breast laterality detection mechanism as described in an embodiment of the invention. The system comprises a scanner 210 configured to perform mammography procedure of a patient 200. A detachable patient parameter identifier 220 is provided in association with the scanner for detecting patient parameters based on which the breast laterality may be identified. The patient parameter detected by the patient parameter identifier 220 is provided to processor 230 to interpret laterality from the patient parameters. The scanner 210 includes components such as a rotatable gantry from where the imaging rays are being exposed and a detector placed along with a breast positioner to detect the rays coming out of the breasts. The patient parameter identifier 220 is provided with an adjusting mechanism so that the patient parameter identifier 220 can be adjusted even after it is attached to the imaging system. In one embodiment, patient parameter identifier 220 is a detachable assembly.

The patient parameter identifier 220 is configured to identify the patient parameter with reference to an axis. In an example, the axis can be fixed as the gantry axis. In another example, the axis may be fixed as the position of the breast being imaged. The patient parameter identifier 220 is attachable to a fixed location on the scanner 210 or on the surroundings of the scanner 210, such as the ceiling or another structure located in the same room. The patient parameter identifier 220 is adjusted to rectify the error generated in determining the laterality due to the gantry rotation.

In an embodiment, the patient parameter identifier 220 is a patient position identifier configured to identify the position of a patient with reference to an axis. If the right breast is being imaged, the rest of the patient body will be laying towards left and if the patient body is detected towards left, the processor 230 is configured to interpret the laterality as "Right".

In an embodiment, the patient parameter identifier 220 is a patient weight measuring assembly configured to detect the distribution of patient weight with respect to an axis. The patient weight measuring assembly determines if the weight of the patient is more towards left or right of an axis. If the patient weight is more towards left, the patient body is lying towards left and the right breast is being imaged, hence the processor is configured to interpret the laterality as "Right" and if the weight is more towards right, the laterality is interpreted as "Left".

In an embodiment, the patient parameter identifier 220 is configured to be a patient head orientation identifier, configured to detect the orientation of the patient head with respect to an axis. This is helpful in determining the laterality in recumbent position. For imaging, the patient will be lying facing the gantry. The patient head orientation identifier is configured to identify the orientation of the patient head, as towards left or right, and based on the same the laterality can be determined. Generally, the breast will be positioned on a breast positioner before imaging. By identifying the position of the breast positioner along with the orientation of the head, the laterality can be determined. If a patient is laying towards right, left breast will be the upper breast and the laterality can be considered as "Left" and if the patient is laying toward left, the right breast will be the upper breast and the laterality can be assumed as "Right". However the laterality is determined based on the assumption that the breast positioner will always be supporting the upper breast of a patient in recumbent position. However the position of the breast positioner may be changed. Alternately if the patient head orientation is identified, the breast laterality may be interpreted with reference to the height of breast from the ground level. The position of the breast positioner can be changed by providing an adjustable breast positioner or by an adjustable patient table.

In an embodiment, the patient parameter identifier 220 is configured to be movable. In an imaging procedure the image gantry rotates to capture the breast image from different angles. The breast positioner also rotates along with the gantry. The patient parameter is obtained with reference to an axis and this axis is set as an imaginary line passing through the center of the breast being imaged. As the breast positioner is being moved, the axis also tend to change and to interpret the laterality, it is required to have to the axis fixed. In an example, the breast position or the axis is fixed by adjusting the patient parameter identifier 210. In an example, the patient position identifier or patient weight measuring assembly is configured to move with reference to the gantry movement to fix the position of the breast as constant. Similarly the height of the patient table on which the patient is laying is adjusted to fix the breast position. Alternately the breast positioner on which the breast is placed for imaging may be adjusted instead of adjusting the patient table.

In an embodiment, a user interface may be provided to incorporate the laterality manually by an operator. The automatic laterality detection may be provided as an optional or additional feature. Different patient parameters can also be detected manually and may be entered using the user interface.

The processor 230 is configured to receive the patient parameter from the patient parameter identifier 220 and the processor 230 includes any hardware based processing mechanism or an algorithm based processing techniques. The processor 230 is configured to interpret the breast laterality based on different patient parameters. The processor 230 may be attached to the patient parameter identifier 220 or with the scanner 210 or it could be an external circuitry.

In an embodiment, the processor 230 is associated with the scanner 210. The processor 230 may be configured to adjust the imaging process or laterality recording process by the scanner 230 based on the laterality detected.

Figure 3A:
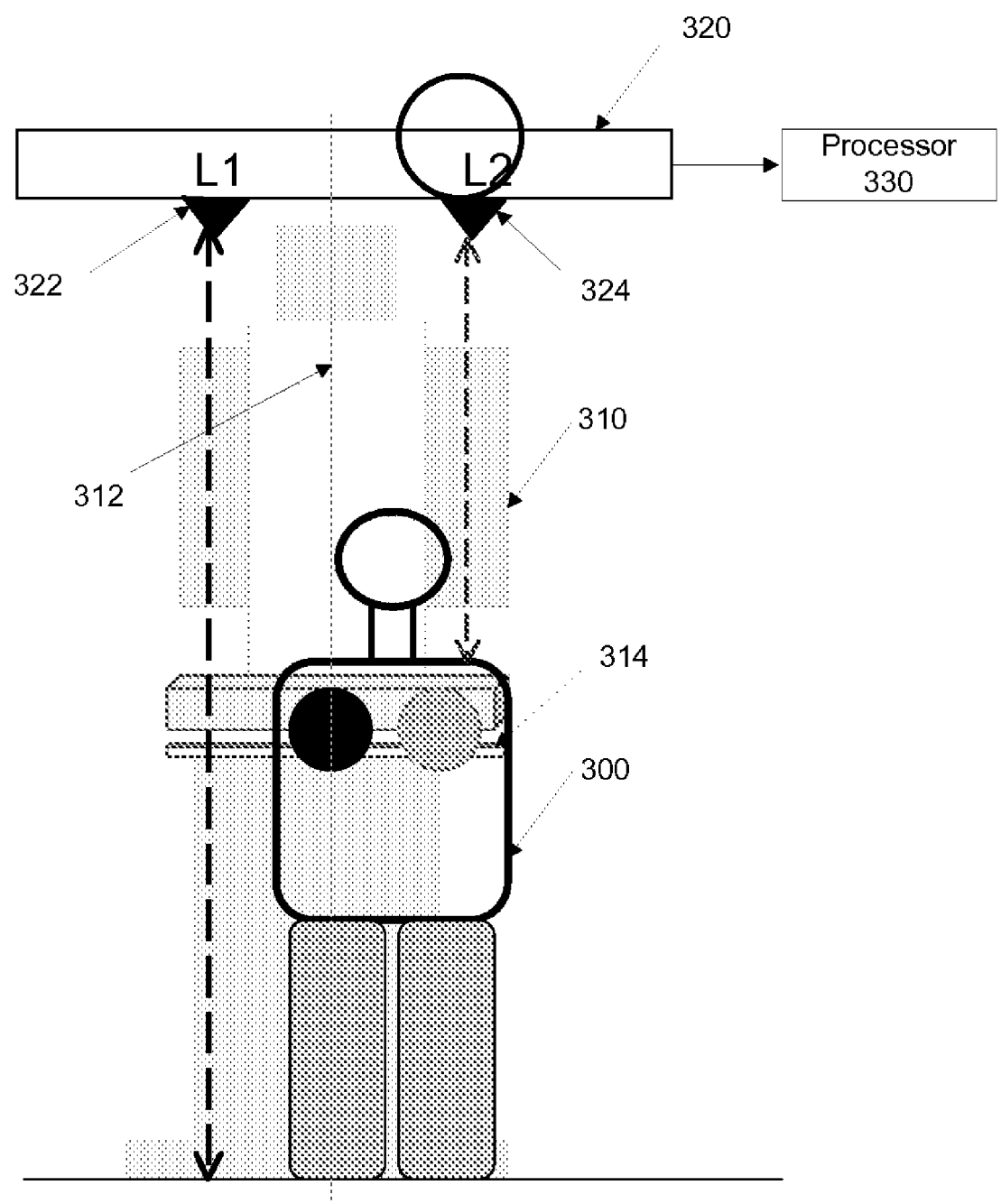
FIGS. 3A and 3B are diagrammatic illustrations of a mammography imaging system with sensor-based automatic breast laterality detection in left and right breast imaging configurations, respectively, as described in an embodiment of the invention.
Figure 3B:
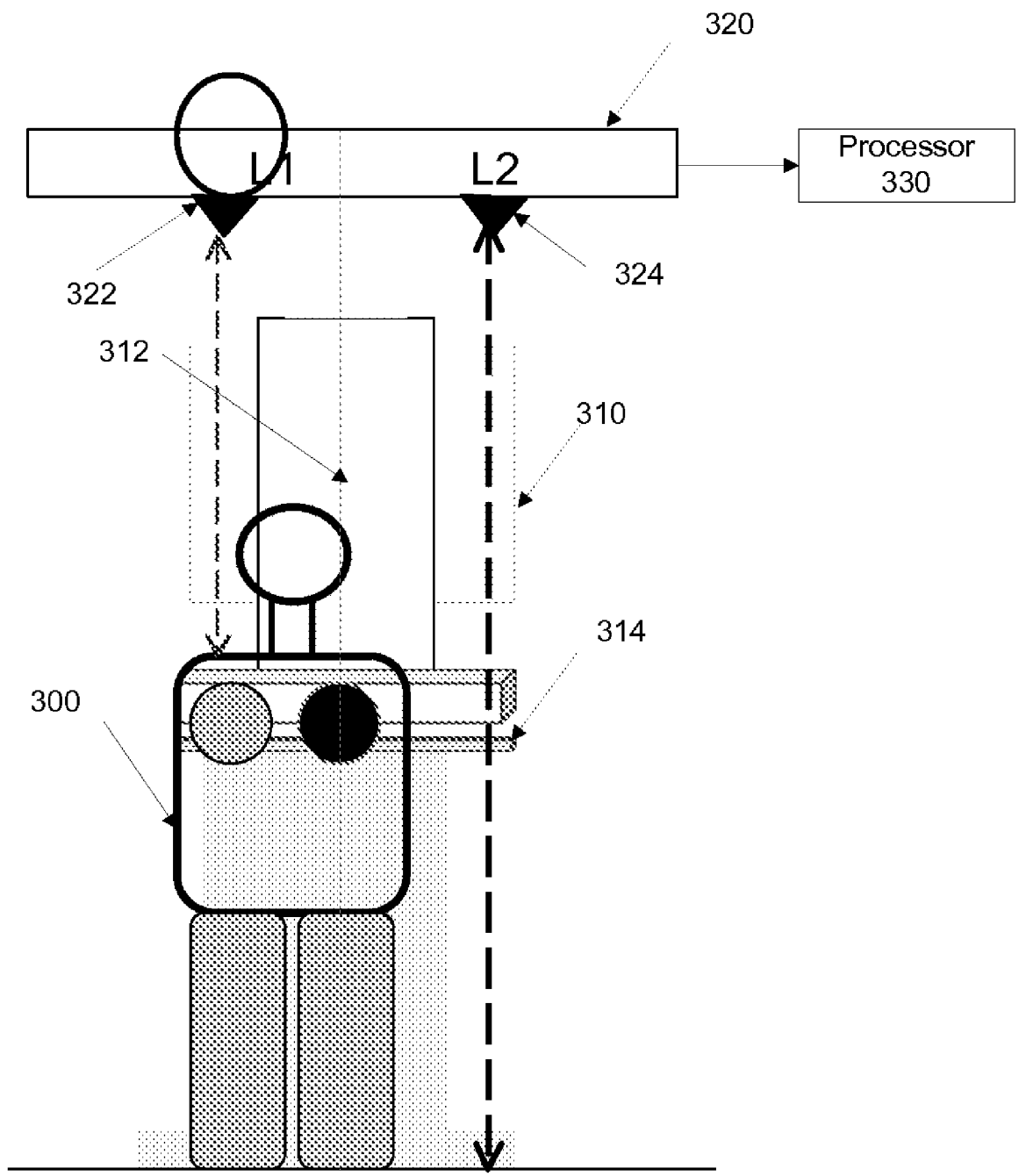

FIGS. 3A and 3B are diagrammatic illustrations of a mammography imaging system with sensor-based automatic breast laterality detection in left and right breast imaging configurations, respectively, as described in an embodiment of the invention. The figures illustrate a sensor-based patient position identifier to detect the position of a patient 300. The imaging system includes a scanner 310 that is configured to include a gantry through which X-ray beams are exposed and a detector to detect the X-rays passing through the breasts. The breast is positioned on a breast positioner and is compressed using a compressor for increasing the quality of the image. A sensor assembly 320 is provided to detect the patient location with reference to an axis. The sensor assembly 320 is a detachable and an adjustable assembly. The sensor assembly 320 can be attached to a fixed location such as a non-moving part of the scanner 310 or some fixed position such as the ceiling above the scanner 310. The sensor assembly 320 could be attached to the upper or lower portion of the scanner 310. In an example, the sensor assembly 320 is attached to the upper portion of the scanner 310. The sensor assembly 320 includes at least one sensor. However the number of sensors used could be decided based on the application. In an example, only one sensor may be used and if the sensor detects a signal the laterality is assumed as one and in the absence of the signal the laterality is determined as the other. The position of the patient is identified with reference to an axis 312. The sensor assembly 320 is configured to detect whether the patient 300 is lying towards right or left with reference to the axis 312. In an example the centre of the breast being imaged is taken as the axis In an embodiment shown, the scanner assembly 320 is provided with two detectors 322, 324 including a left side sensor 322 and a right side sensor 324. If the left sensor 322 detects a signal from the patient's body 300, the patient's body 300 is lying towards left and the laterality is interpreted as "Right" and if the right sensor 324 detects the signal the laterality is assumed as "Left". A processor 330 is provided in association with the scanner and receives the signal from the sensor assembly 320. The processor 330 is configured to interpret laterality as right or left depending upon the signal from right or left sensor.

Different kinds of sensors and different configuration of arrangement could be used in determining the laterality. In an example, an LED based sensor mechanism is used. However the sensors need not be limited to this. Further the expression "sensor" is synonymous with transducer, detecting element, position identifier etc.

In an embodiment, the sensor assembly 320 is attached to the lower end of the scanner 310. The sensor assembly 320 may be attached at the pedal or stand, where the patient will be standing for imaging. The sensor assembly 320 may be configured to detect the point of contact of the feet on the pedal and based on the same the laterality may be determined. FIG. 3A shows that the patient's left breast is being imaged and FIG. 3B shows that patient's right breast is being imaged. The patient 300 in the figures are shown sitting or standing position facing the scanner 310 or the gantry.

However since the gantry of the scanner 310 moves while imaging, the breast position may not remain fixed for a particular gantry angle. Generally while imaging the patient 300, the breast is being positioned on a breast positioner 314 and the breast positioner 314 also rotates with gantry movement. Also many times a magnification stand (not shown) is placed on the breast positioner 314 to magnify the image. This also varies the breast position or the height at which the breast is placed from the ground level. Since the breast position is not constant, the axis with reference to which the position of the patient is determined also varies and this results in an error in the laterality measurement. A method for correcting the error or fixing the breast position is illustrated with reference to FIG. 4.

Figure 4:
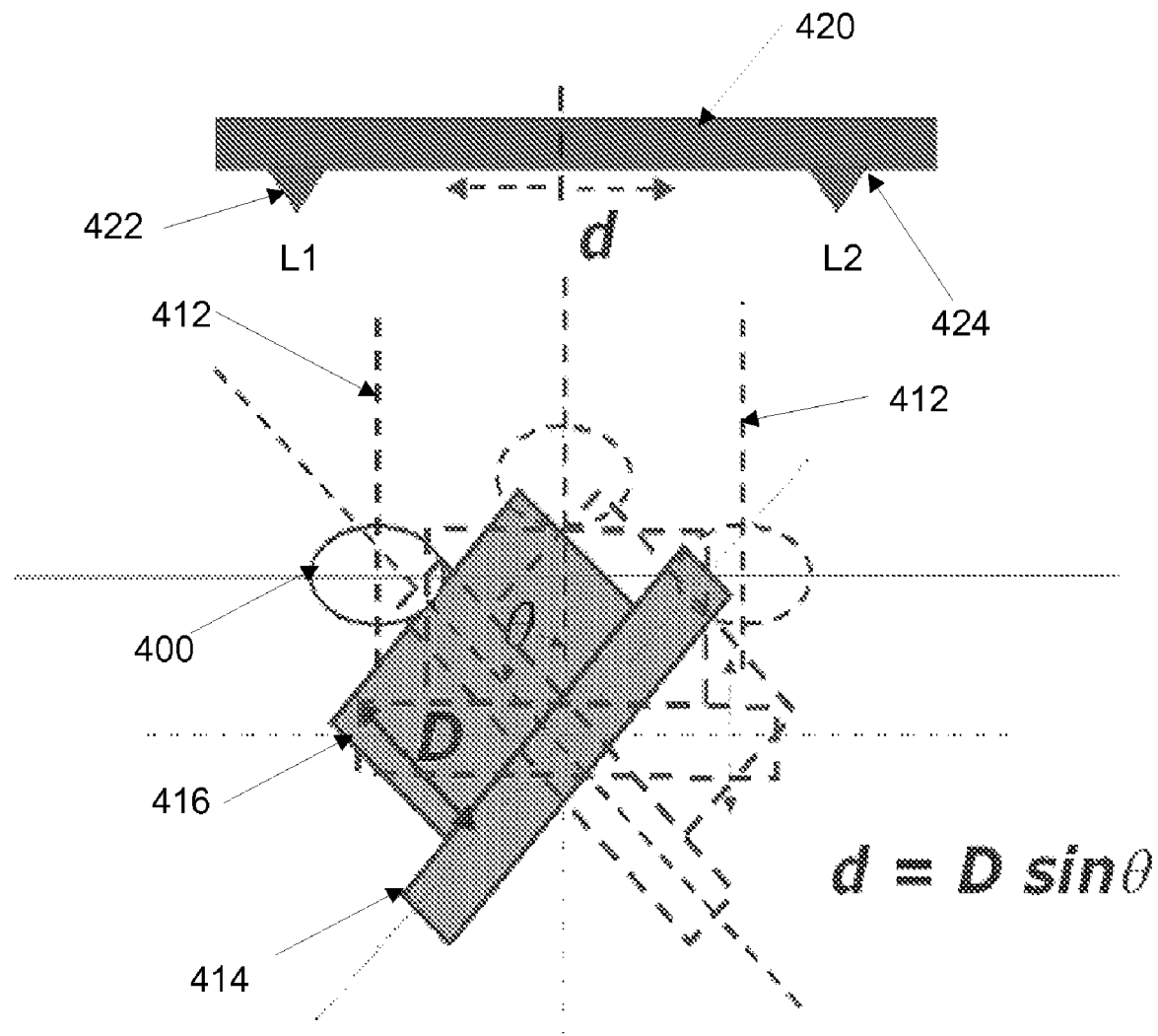
FIG. 4 illustrates a schematic diagram of a breast position error correction technique as described in an embodiment of the invention.

FIG. 4 illustrates a schematic diagram of a breast position error correction technique as described in an embodiment of the invention. In an embodiment shown, the error is eliminated by moving the sensor assembly 420 with respect to the gantry movement or gantry angle. The sensor assembly 420 is provided with two sensors 422 and 424. The axis based which the breast position s determined is indicated as 412. To calculate the distance to which the sensor assembly 420 needs to be displaced, it is required to find the changes in the breast position 400 due to the gantry movement. For obtaining the breast position 400 changes, consider measuring the height of patient breast from a breast positioner 414, indicated as "D". If a magnification stand 416 is provided the height of the magnification stand 416 is also considered. Thus the height "D" is measured and the angle at which the gantry rotates is also obtained. Based on these two factors the amount to which the sensor assembly 420 needs to be adjusted or displaced is calculated. The displacement required for the sensor assembly 420 expressed as "d" is obtained by using a formula given below:

$$d = D \sin \theta$$

Thus based on the gantry angle, the sensor assembly 420 is moved to fix the position of the axis 412 or the breast position 400.

Similar other techniques may be used in correcting the error, for example instead of moving the sensor assembly the breast positioner on which the breast is positioned or the table/chair on which the patient is laying/sitting may be adjusted.

Figure 5A:
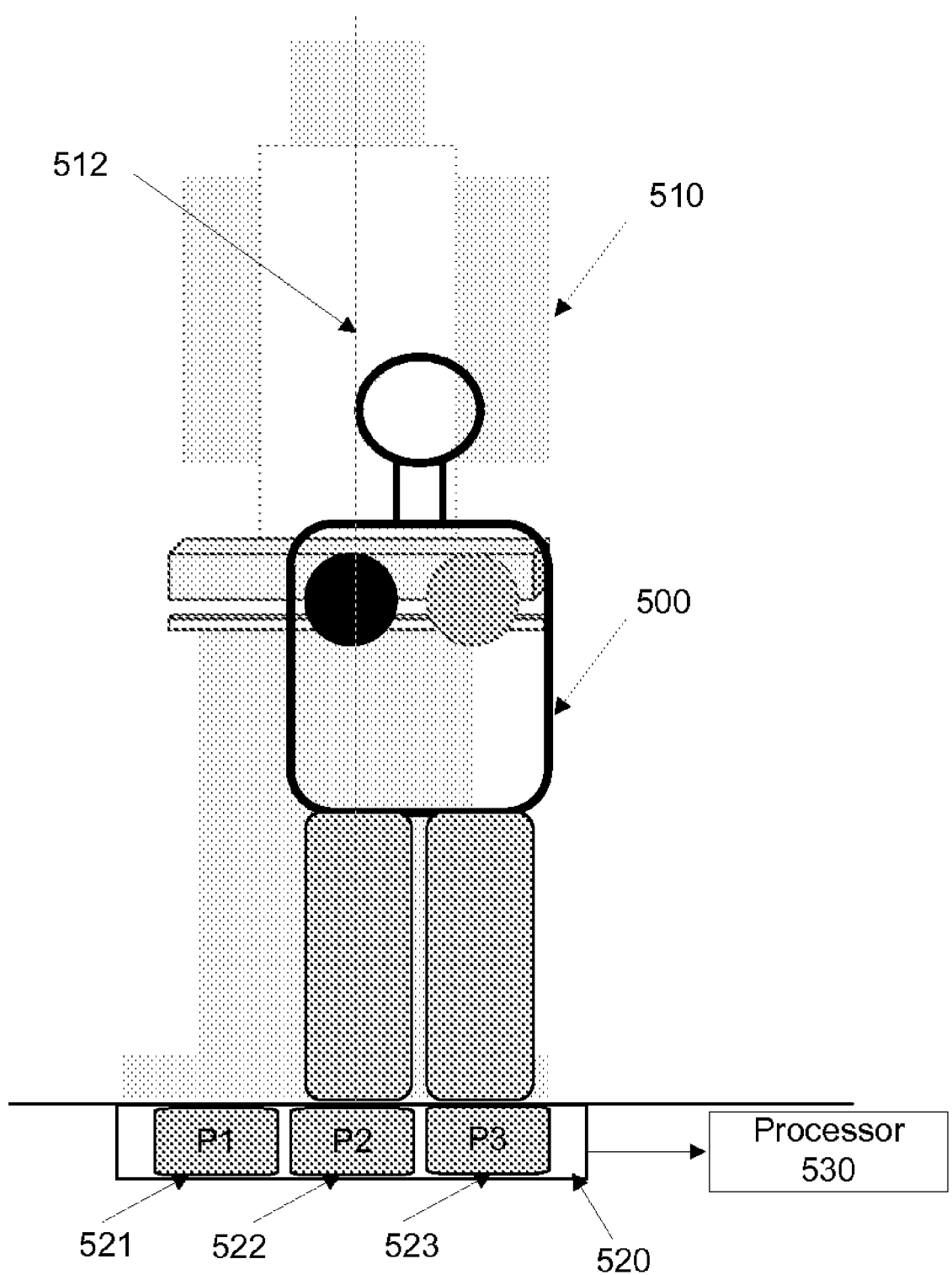
FIGS. 5A and 5B are diagrammatic illustrations of a mammography imaging system with pedal-based automatic breast laterality detection in left and right breast imaging configurations, respectively, as described in an embodiment of the invention.
Figure 5B:
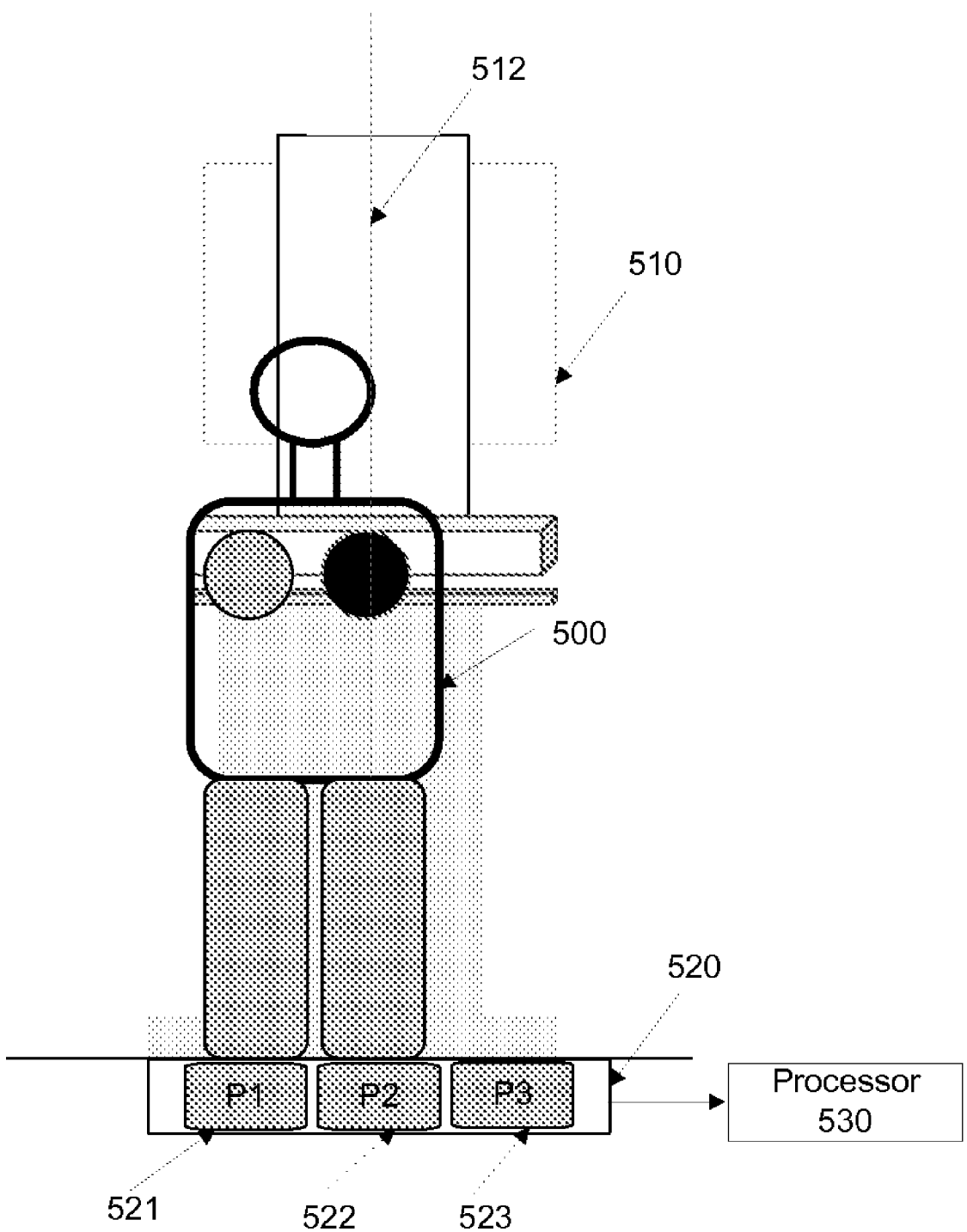

FIGS. 5A and 5B are diagrammatic illustrations of mammography imaging system with pedal-based automatic breast laterality detection in left and right breast imaging configurations, respectively, as described in an embodiment of the invention. A patient 500 is configured to stand in front of a scanner 510 for imaging. A weight measuring assembly provided as patient parameter identifier. The weight measuring assembly is defined such that it is capable of indicating the weight distribution of a patient with reference to an axis 512 i.e. to indicate whether the weight is more towards left side or towards right side. In an example, the axis is defined as an imaginary line passing through the center of the breast being imaged. In an example, a pedal assembly 520 is provided as attachable to the scanner 510 for the patient to stand in front of the imaging system for imaging. The pedal assembly 510 may use weight sensitive pedals to detect the weight of the patient or pedal assembly 520 may be associated with a separate weight measuring mechanism. The pedal assembly 520 is provided with three pedals 521,522,523 and at the time of imaging left or right breast, the patient uses only two pedals. The patient uses adjacent two pedals at a time. If the patient's right side is being imaged, the patient 500 will be using the two pedals towards the left i.e. pedals 521 and 522 and based on the same a processor 530 interprets the laterality. Similarly if the left side of the patient 500 is being imaged the patient 500 will use the two pedals towards the right i.e. pedals 522 and 523 and based on this information the processor 530 interprets the laterality as "Left". Similar other configurations of weight measuring assembly may be used and need not be limited to pedal assembly 520. FIG. 5A shows that the patient's left breast is being imaged and FIG. 5B shows that patient's right breast is being imaged.

Similar to while using sensor assembly 320, there could be an error generated in the determination of laterality due to the gantry rotation. This could be rectified by adjusting the pedal assembly 520 with respect to the gantry angle. Instead of physically changing the position of the pedal assembly 520 some kind of algorithmic correction may be applied to adjust the position of the pedal assembly 520, before determining the laterality.

Figure 6A:
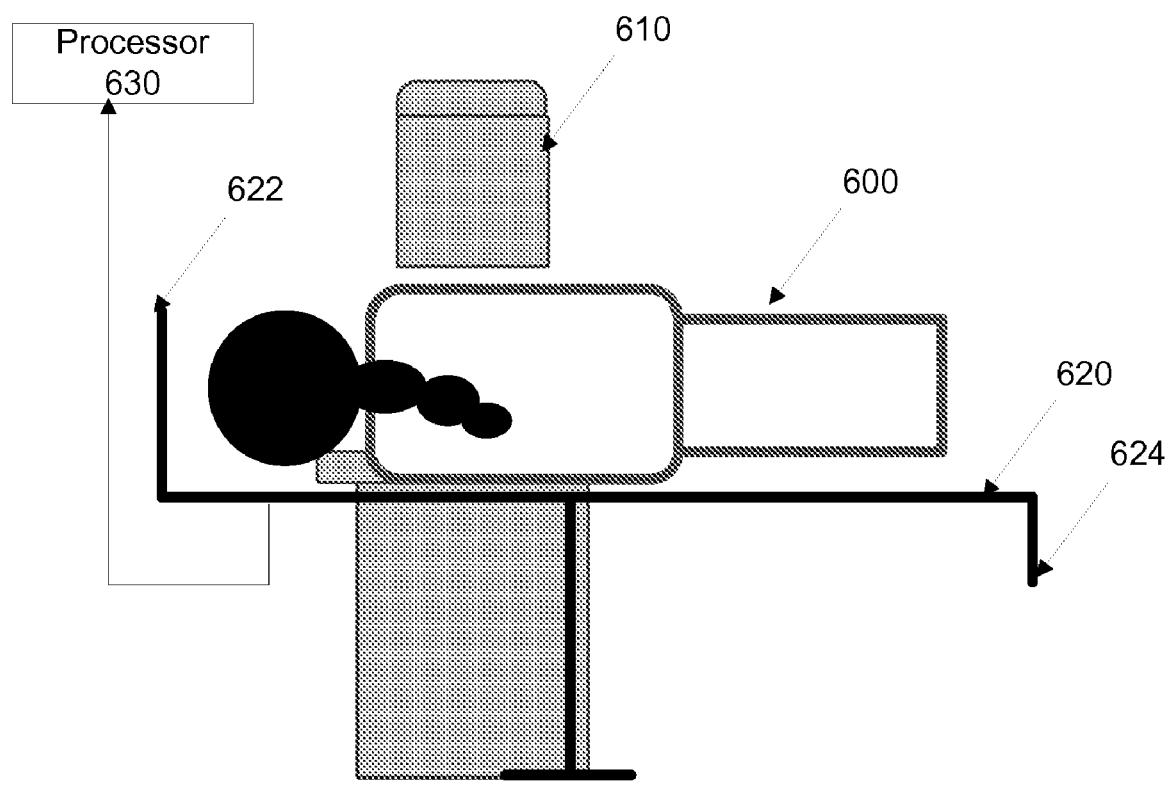
FIGS. 6A and 6B are diagrammatic illustrations of a mammography imaging system with patient table-based automatic breast laterality detection in left and right breast imaging configurations, respectively, as described in an embodiment of the invention.
Figure 6B:
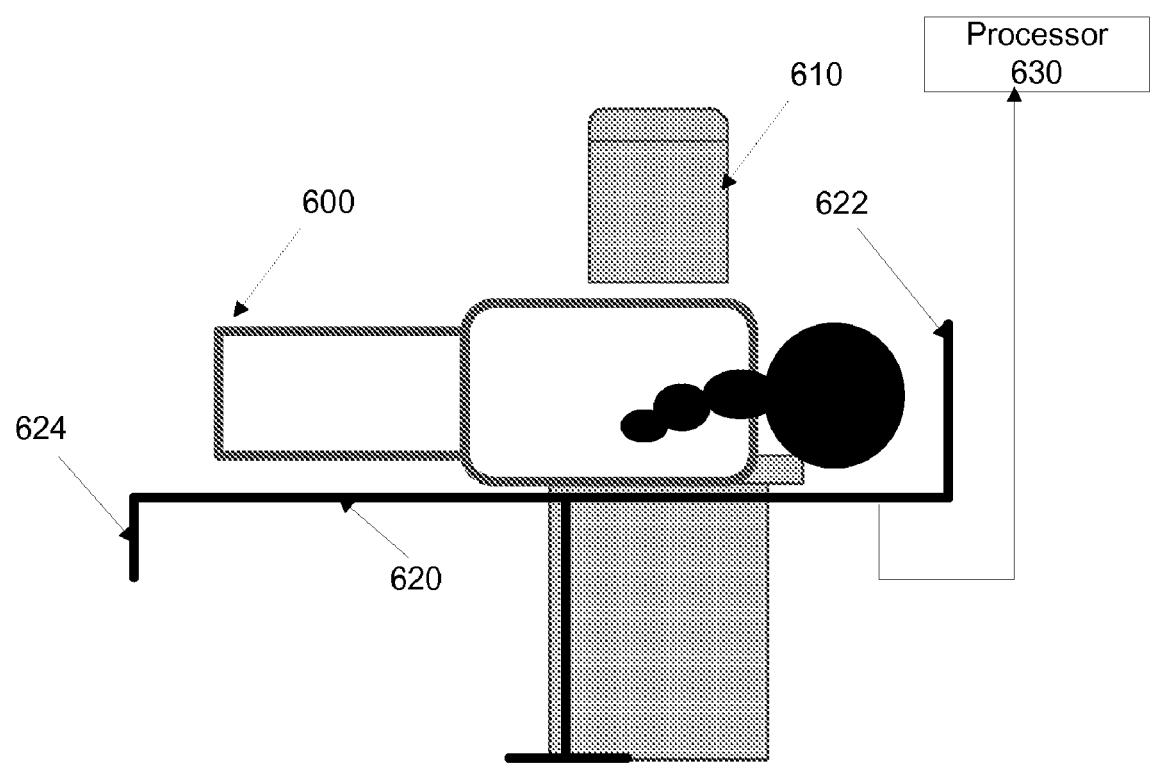

FIGS. 6A and 6B are diagrammatic illustrations of a mammography imaging system with patient table-based automatic breast laterality detection in left and right breast imaging configurations, respectively, as described in an embodiment of the invention. A patient head orientation identifier is provided as the patient parameter identifier. Laterality of patient 600 in the recumbent position is determined using this technique. The patient 600 is supposed to lie down in front of an imaging system 610 for imaging. The breast being imaged is supported by a breast positioner (not shown). The patient location may also be identified along with the orientation of the patient head. In an embodiment, the patient's head orientation may be obtained by using a patient table 620. As and when the patient table 620 is attached to the imaging system 610, the imaging system 610 is configured to identify that the patient is in recumbent position i.e. the head is not in straight position. The other possible orientation is head is oriented towards left or right. The patient table 620 may provided with a mechanism to identify the orientation of the patient. In an example, the patient table 620 could be provided with head end 622 and tail end 624 and by detecting the same the orientation of the patient head can be identified. To define the head end and the tail end, the patient table 620 could be provided with a header or footrest etc. In an example, the patient table 620 could be rotatable patient table, based on the degree of rotation, the head orientation may be identified. In an example, if the table is at 0 degree on it vertical axis, the head orientation is taken as towards left as shown in FIG. 6A. If the patient table 620 is at 180 degree on its vertical axis, the head orientation is taken right, as shown in FIG. 6B. Based on the patient table's degree of rotation the head orientation is obtained. A processor 630 is configured to interpret the laterality based on the head orientation information. Based on the head orientation the laterality may de determined. If the patient head is oriented towards right, the laterality may be assumed as "Left" and if the patient 600 is lying towards left, the laterality is interpreted as "Right". While determining the laterality it is assumed that breast positioner will be holding or supporting the upper breast, the breast that is away from the patient table 620 while the patient 600 is lying. The head orientation again is determined with reference to an axis. In an example, the axis is an imaginary line passing through the center of the breast being imaged.

FIGS. 7A to 7D illustrate various positions of an adjustable patient table and laterality table indicating the laterality based on the table position, as described in an embodiment of the invention. In the figures shown, the table is positioned such that the table is at zero degree rotation with respect to vertical axis and head end is towards right. The patient table is configured to be located at three different levels including level 1, level 2 and level 3 from the ground level. Level 1 is the lowest level, level 3 is the highest level and level 2 is the intermediate height level. At FIG. 7A the patient table is at the lowest position i.e. at Level 1. The patient head is oriented towards left, which is obtained from the position of the patient table and it is assumed that the breast positioner is not moving with reference to the patient table. Initially the breast positioner is set at a particular height, such that the upper breast is supported when the patient table is at a prefixed height. At level 1, it is assumed that the breast positoner is supporting the upper breast and based on the head orientation the laterality is interpreted as "Right". At FIG. 7B the patient table is at level 2. The breast positioner supports both the breasts equally or the breast positioner is at equal distance from both the breasts. Here both the breasts can be imaged simultaneously and the laterality can be interpreted as both. At FIG. 7C the patient table is at Level 3 or the table is at the highest level from the ground level. The breast positioner will be supporting the lowest breast and since the head orientation is toward left, the laterality can be interpreted as "Left". FIG. 7D shows a table illustrating the laterality based on the head orientation and different patient table heights.

FIGS. 8A to 8D illustrates various positions of an adjustable patient table and laterality table indicating the laterality based on the table position as described in an embodiment of the invention. In the figures shown, the table is positioned such that the table is at 180 degree rotation with respect to vertical axis and head end is towards right. The patient table is configured to be located at three different levels including level 1, level 2 and level 3. Level 1 is the lowest level and level 3 is the highest level and level 2 is the intermediate height level. At FIG. 8A the patient table is at the lowest position i.e at Level 1. The patient head is oriented towards right, which is obtained from the position of the patient table and it is assumed that the breast positioner is not moving with reference to the patient table. Initially the breast positioner is set at a particular height, such that the upper breast is supported when the patient table is at a prefixed height. At level 1, it is assumed that the breast positoner is supporting the upper breast and based on the head orientation and the laterality is interpreted as "Left". At FIG. 8B the patient table is at level 2. The breast positioner supports both the breasts equally or the breast positioner is at equal distant from both the breasts. Here both the breast can be imaged simultaneously and the laterality can be interpreted as both. At FIG. 8C the patient table is at Level 3 or the table is at the highest level from the ground level. The breast positioner will be supporting the lowest breast and since the head orientation is toward right, the laterality is interpreted as "Right". FIG. 8D shows a table illustrating the laterality based on the head orientation and different patient table heights.

Figure 9A:
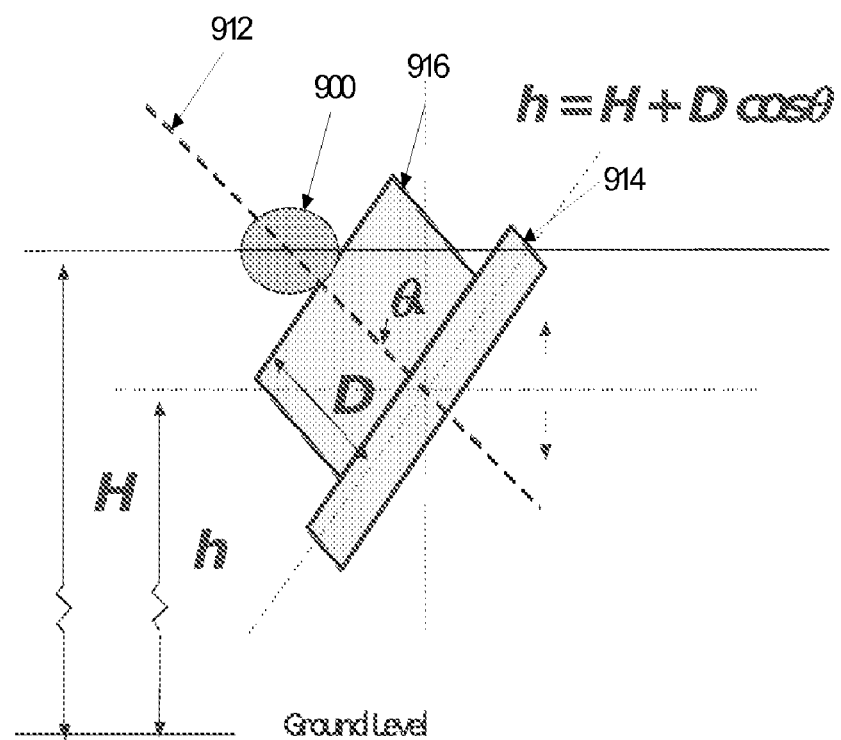
FIGS. 9A and 9B illustrate schematic diagrams of a breast position error correction technique as described in an embodiment of the invention.
Figure 9B:
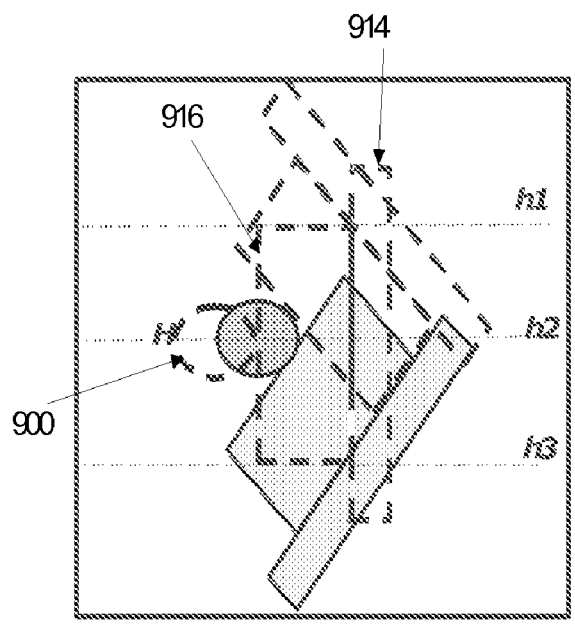

FIGS. 9A and 9B illustrate schematic diagram of a breast position error correction technique as described in an embodiment of the invention. In FIG. 9A, the breast 900 of patient being imaged is placed on a breast positioner 914. A magnification stand 916 is placed on the breast positioner 914. The laterality is determined with reference to an axis 912 and the axis 912 is fixed as an imaginary line passing through the center breast 900. While scanning, the gantry rotates and with reference to that the breast positioner 914 and the magnification stand 916 also rotate. However to determine the laterality correctly, the axis 912 needs to be fixed and for this the breast position needs to be fixed. It is assumed that the breast 900 is located at fixed height "H" from the ground level. The breast positioner height is at "h" from ground level. The distance between the breast and actual axis of rotation is represented as "D" and this may vary based on the usage of magnification stand 916. In an embodiment, the height of the breast positioner "h" is adjusted with reference to the gantry angle, so that breast is maintained at a fixed height from the ground level. The height at which the positioner need to be located to fix the breast position is given by the following formula $$h = H + D \cos \theta$$

Thus the breast height H may be fixed by varying the positioner height "h". In this embodiment the patient table height can be fixed or variable. FIG. 9B shows the breast positioner at different heights indicated as h1, h2 and h3.

Alternately the patient table may be adjusted to fix the patient's breast position.

Figures 10A, 10B:
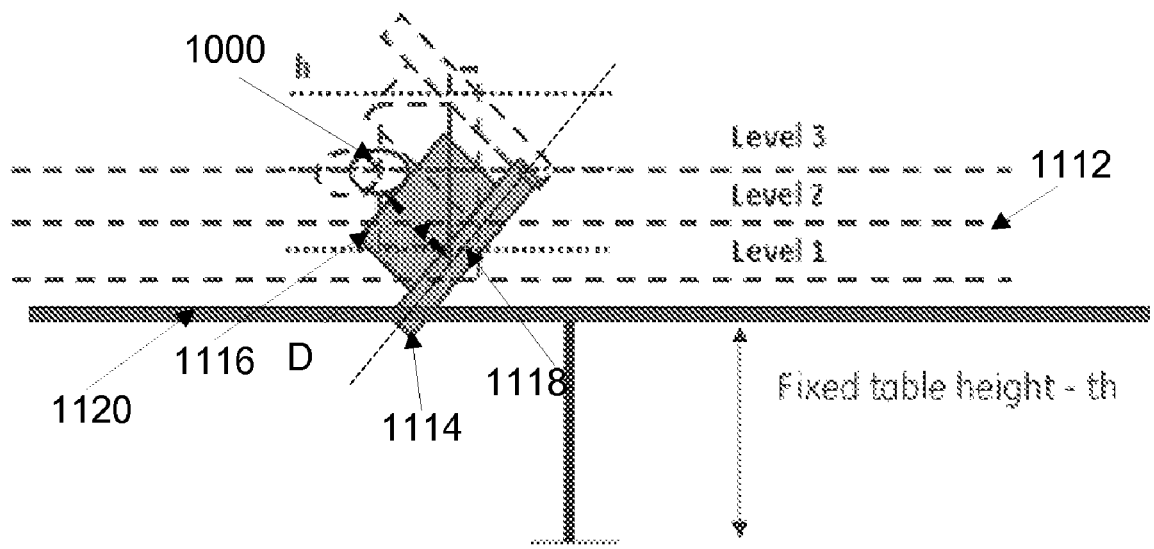
FIG. 10A illustrates a schematic diagram for determining laterality of breast in a mammography procedure as described in an embodiment of the invention.
FIG. 10B shows a table illustrating the laterality identified based on the embodiment illustrated in FIG. 10A.

FIG. 10A illustrates schematic diagram for determining laterality of breast in a mammography procedure as described in an embodiment of the invention. In the figure, the patient table height is fixed at a given time. The breast 1000 of patient being imaged is placed on a breast positioner 1014. A magnification stand 1016 may be placed on the breast positioner 1014. The laterality is determined with reference to one of three axes 1012 shown in the figure. The axes 1012 are fixed with reference to the patient table 1120. In an embodiment, the current axis 1012 is defined based on the breast positioner height "h" from the ground level and the gantry angle "θ" for a fixed table height and distance "D" between the axis 1012 and gantry axis 1018. The current axis height "H" is calculated as follows:

$$H = h - D \cos \theta$$

Thus in this embodiment, the axis is selected based on the breast positioner height and the gantry angle.

FIG. 10B shows a table illustrating the laterality identified based on the embodiment illustrated in FIG. 10A. Based on the value of H, the laterality is determined from FIG. 10 B.

The advantages of the invention include minimizing the human intervention in detecting the breast laterality. It improves the mammography imaging workflow. Some of the solutions may be implemented without making any hardware changes to the existing scanner or the patient table.

The above-description of the embodiments of the methods and systems has the technical effect of automatically interpreting laterality from different patient parameters.

Thus various embodiments of the invention describe a method and system for automatically determining the laterality of breasts in a mammography imaging procedure.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Exemplary embodiments are described above in detail. The assemblies and methods are not limited to the specific embodiments described herein, but rather, components of each assembly and/or method may be utilized independently and separately from other components described herein. Further the steps involved in the workflow need not follow the sequence in which there are illustrated in figures and all the steps in the work flow need not be performed necessarily to complete the method.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A mammography imaging system with automatic laterality detection comprising:
   a scanner;
   a detachable, patient parameter identifier attached to the scanner, the patient parameter identifier configured to detect a patient parameter based on the orientation of a patient with respect to an axis; and
   a processor configured to interpret breast laterality based on the patient parameter.

2. A system as in claim 1, wherein the patient parameter identifier is a patient position identifier attachable to a fixed location.

3. A system as in claim 1, wherein the patient parameter identifier is an adjustable weight measuring assembly attachable to a lower portion of the scanner and configured to indicate the weight distribution of the patient.

4. A system as in claim 1, wherein the patient parameter identifier is a patient head orientation identifier attachable to the imaging system.

5. A system as claimed in claim 1, wherein the processor is further configured to perform an error correction by moving at least one of the patient parameter identifier with reference to the gantry movement, keeping center of the breast position as the axis.

6. A mammography imaging system with automatic laterality detection comprising:
   a scanner;
   a detachable sensor assembly having one or more sensors attached to the scanner, and configured to detect the position of a patient with reference to an axis; and
   a processor configured to interpret laterality of the patient based on the position of the patient.

7. A system as in claim 6, wherein the sensor assembly comprises two sensors, each sensor located to identify right and left side of the patient, respectively.

8. A system as in claim 7, wherein the sensor positioned at one side is configured to generate a signal while other side of the patient is being imaged.

9. A mammography imaging system with automatic laterality detection comprising:
   a scanner;
   a patient weight measuring assembly attachable to the scanner, and configured to detect the distribution of a patient's weight with respect to an axis; and
   a processor configured to interpret laterality of the patient based on the weight distribution of the patient.

10. A system as in claim 9, wherein the patient weight measuring assembly includes a pedal assembly having at least three pedals, and wherein any two adjacent pedals are configured to be stood on by the patient at a time.

11. A mammography imaging system with automatic laterality detection comprising:
    a scanner having an adjustable breast positioner;
    an adjustable patient table attachable to the scanner, providing direction of head of a patient and location of a patient with reference to ground level;
    and a processor configured to interpret laterality of the patient based on the orientation of the patient.

12. A system as in claim 11, wherein the breast positioner is configured to change its position in response to the scanner movement, with reference to an axis.

13. A system as in claim 11, wherein the patient table is configured to position the patient at different heights from ground level.

14. A system as in claim 11, wherein the processor is configured to determine the laterality based on at least one of patient table height with reference to ground level, patient head direction, and breast position with reference to the breast positioner.

15. A system as in claim 11, wherein the processor is configured to perform an error correction by moving at least one of the patient table or breast positioner with reference to the gantry movement, keeping center of the breast position as the axis.

* * * * *